United States Patent [19]

Sias

[11] 3,931,265

[45] Jan. 6, 1976

[54] PROCESS FOR PRODUCING ANIONIC METAL-CONTAINING SULFONATES

[75] Inventor: Roy C. Sias, Ponca City, Okla.

[73] Assignee: Continental Oil Company, Ponca City, Okla.

[22] Filed: Nov. 12, 1973

[21] Appl. No.: 415,285

Related U.S. Application Data

[63] Continuation of Ser. No. 240,273, March 31, 1972, abandoned.

[52] U.S. Cl. .............. 260/440; 252/33.4; 252/33; 260/429 K; 260/448.2 N; 260/448.8 AS; 260/462; 260/503; 260/563; 260/606.5 P; 260/607; 260/920
[51] Int. Cl.² .......................................... C07F 9/68
[58] Field of Search........ 260/440, 429 K; 252/33.4, 252/33

[56] References Cited

UNITED STATES PATENTS

| 2,451,549 | 10/1948 | Gzemski | 260/439 R |
|---|---|---|---|
| 2,760,970 | 8/1956 | Le Suer | 260/439 R |
| 2,809,209 | 10/1957 | Voorhees | 260/439 R |
| 2,824,126 | 2/1958 | Bray | 260/429 R |
| 3,025,259 | 3/1962 | Sheldahl | 252/33 |
| 3,192,158 | 6/1965 | Bergstrom | 252/33.4 |

FOREIGN PATENTS OR APPLICATIONS 871,144   6/1961   United Kingdom............ 260/439 R

OTHER PUBLICATIONS

Heslop et al., Inorganic Chemistry, Elsevier Publishing Co., New York, N.Y., 1967, pp. 459, 461.

Primary Examiner—Arthur P. Demers
Attorney, Agent, or Firm—Robert B. Coleman, Jr.

[57] ABSTRACT

A process for producing oil-soluble anionic metal sulfonates is disclosed wherein an anionic metal acid anhydride or its corresponding hydrate is reacted with an oil-soluble sulfonic acid and a polyamine compound to produce the desired metal sulfonate. The metal constituent of the anionic metal acid anhydride is selected from the group consisting of silicon, molybdenum, vanadium, arsenic, phosphorus, selenium, boron and tellurium.

12 Claims, No Drawings

PROCESS FOR PRODUCING ANIONIC METAL-CONTAINING SULFONATES

This is a continuation, of application Ser. No. 240,273, filed Mar. 31, 1972, now abandoned.

This invention relates to oil-soluble anionic metal sulfonates. In one aspect the invention relates to oil-soluble anionic metal sulfonates wherein the metal constituent is selected from silicon, molybdenum, vanadium, phosphorus, arsenic, selenium, boron and tellurium. In another aspect the present invention relates to a process for producing oil-soluble anionic metal sulfonates from acid anhydrides of silicon, phosphorus, molybdenum, vanadium, arsenic, selenium, boron and tellurium and oil-soluble sulfonic acids and polyamine compounds.

In recent years it has been found that superior standards for spectrographic equipment can be prepared from oil-soluble metal sulfonates and metal dispersions in such sulfonates by dissolving such materials in predetermined quantities in a suitable solvent. Such standards have exhibited indefinite shelf life and any combination of metals can be combined without precipitation of the metal constituents.

Further, dispersions containing certain oil-soluble metal sulfonates have acquired considerable importance as additives in fuels and lubricating oil. Such dispersions have been highly useful as additives to other materials where the problem of suspending insoluble waste materials formed in the utilization of the material and also the problem of corrosion inhibition is met. When the oil-soluble metal sulfonates are employed as additives for use in internal combustion engine lubricating compositions, such agents function to effectively disperse or peptize the insolubles formed by the fuel combustion, oil oxidation, or similar conditions obtained during the operation of the engine.

Thus, while the use of oil-soluble anionic metal sulfonates have been established and recognized, problems have been encountered in the production of oil-soluble anionic metal sulfonates of certain metals, such as molybdenum, arsenic and vanadium. Therefore, a need has long been recognized for an improved process for the production of oil-soluble anionic metal sulfonates from readily available chemical compounds, and it is to such a process that the present invention is directed.

An object of the present invention is to provide an improved process for the production of oil-soluble anionic metal sulfonates. Another object of the present invention is to provide an economical, dependable, and efficient method for preparing oil-soluble anionic metal sulfonates from readily available chemical compounds.

Another object of the present invention is to provide an improved method for the preparation of oil-soluble anionic metal sulfonates of silicon, molybdenum, vanadium, phosphorus, arsenic, selenium, boron and tellurium which are suitable as analytical standards while at the same time providing an oil-soluble source of such metals.

These and other objects, advantages, and features of the present invention will be apparent to those skilled in the art from a reading of the following detailed description.

According to the present invention, I have found a process for producing oil-soluble anionic metal sulfonates wherein the metal constituent is selected from silicon, molybdenum, vanadium, phosphorus, arsenic, selenium, boron and tellurium which comprises admixing an acid anhydride compound of such metals with an oil-soluble sulfonic acid and a polyamine compound, heating the resulting mixture to its reflux temperature for a period of time effective to allow formation of the oil-soluble metal sulfonate.

Further according to the invention I have found that it is desirable for said acid anhydride and said sulfonic acid to be present in a stoichiometric amount in a ratio of from about 10:1 to about 1:20 respectively with said polyamine compound. A volatile inert solvent can be incorporated with the oil-soluble sulfonic acid to reduce the viscosity of same and to facilitate the admixing of the oil-soluble sulfonate with said acid anhydride and said polyamine compound.

Oil-soluble metal sulfonates have been recognized as desirable analytical standards as well as oil-soluble additives for fuels and lubricants. However, problems have been encountered in producing oil-soluble anionic metal sulfonates such as molybdenum sulfonate, arsenic sulfonate and vanadium sulfonate.

I have now found that oil-soluble anionic metal sulfonates of silicon, molybdenum, vanadium, phosphorus, arsenic, selenium, boron and tellurium can readily be prepared by reacting an acid anhydride compound of such metal with an oil-soluble sulfonic acid and a polyamine compound at elevated temperatures for a period of time effective to allow said acid anhydride compound to react with said oil-soluble sulfonic acid and said polyamine compound to produce the desired oil-soluble anionic metal sulfonate.

The present invention can be carried out as either a batch process or a continuous process. However, for the sake of simplicity the process of the present invention will be described as a batch process.

The metal acid anhydride, the polyamine compound and the oil-soluble sulfonic acid are charged to a reaction vessel equipped with heating means, a stirring means and a reflux means. Generally, it is desirable to introduce an effective amount of an inert volatile solvent to the reaction mixture to reduce the viscosity of the oil-soluble sulfonic acid thereby facilitating the mixing and contact between the reactants. The amount of inert volatile solvent employed can vary widely depending upon the viscosity of the particular oil-soluble sulfonic acid employed as well as the viscosity desired in the reaction mixture but will generally be in an amount ranging from about 5 to 75 weight percent, based on the weight of the reaction mixture. The amount of the reactants can vary widely, however, the metal acid anhydride and sulfonic acid should be present in a stoichiometric amount with the polyamine compound. Generally, the acid anhydride and sulfonic acid should be present in a stoichiometric amount in a ratio of from about 10:1 to about 1:20 respectively.

It is important in the operation of the present invention that a sufficient amount of sulfonic acid be employed to neutralize at least one amine group of the polyamine compound and that sufficient acid anhydride be employed to react with the remaining amine group or groups of the polyamine compound. It may be found that with certain polyamine compounds, to maintain suitable oil solubility, enough sulfonic acid to neutralize two amine groups of the polyamine compound should be employed, although, at least one amine group of the polyamine compound should be left available to react with the acid anhydride.

Once the reactants have been introduced into the reaction vessel, the reactants are thoroughly agitated and the reaction mixture is heated to its reflux temperature which will generally be within the range of about 60° to 125° C. When the reaction mixture reaches its reflux temperature, it is maintained at such temperature under reflux conditions for an effective period of time to allow the reactants to react and form the desired oil-soluble anionic metal sulfonate. The reflux time of the reaction mixture can vary widely but will generally range from about 0.5 to about 12 hours. It is often desirable to introduce to the mixture prior to same being refluxed from about 5 to 75 weight percent water based on sulfonic acid. Further, it has also been found desirable to introduce to the mixture prior to same being refluxed from about 50 to 300 weight percent of a high boiling alcohol based on sulfonic acid. In the operation of the present invention in some instances it will be desirable to employ two or more reflux steps at graduated temperatures.

After the above-described reflux steps have been carried out, the mixture is stripped of the volatile components. Any suitable method for removing the volatile components can be employed such as heating the mixture to a temperature from about 125° to 175° C. From about 10 to 300 weight percent of a nonvolatile organic carrier component (based on sulfonic acid) is introduced at any convenient point, such as during the reflux period. Residual volatile material is removed by any suitable means such as vacuum stripping or stripping said mixture with a gas such as nitrogen, carbon dioxide, air and the like for a period of time ranging from 0.2 to 6 hours. The stripped product normally is clarified by filtration of the stripped product through a desirable inert absorbent such as alumina, diatomaceous earth, pumice and the like.

The term "metal acid anhydride" as used herein should be read to include the corresponding hydrated form of the metal acid anhydrides that are suitable for use in the present invention. The metal acid anhydrides which may be employed in the production of the oil-soluble anionic metal sulfonates of the present invention can be any suitable acid anhydride of silicon, molybdenum, vanadium, phosphorus, arsenic, selenium, boron and tellurium and their corresponding hydrates. Examples of such acid anhydrides include $As_2O_5$, $MoO_3$, $SiO_2$, $3SiO_2 \cdot H_2O$, $H_2SiO_3$, $H_4SiO_4$, $V_2O_5$, $HVO_3$, $P_2O_5$, $P_2O_4$, $P_2O_3$, $H_3PO_4$, $SeO_2$, $H_2SeO_3$, $H_3BO_3$, $B_2O_3$, $H_2TeO_4$ and the like. Especially desirable results have been obtained wherein the metal acid anhydride is arsenic acid anhydride ($As_2O_5$). In addition, mixtures of various metal acid anhydrides can be employed.

Suitable oil-soluble hydrocarbon sulfonic acids include alkane sulfonic acid, aromatic sulfonic acid, alkaryl sulfonic acid, aralkyl sulfonic acid, and the natural petroleum mahogany sulfonic acids. The mahogany sulfonic acids include any of those materials which may be obtained by concentrated or fuming sulfuric acid treatment of petroleum fractions, particularly the higher boiling lubricating oil distillates and white oil distillates. The higher molecular weight petroleum oil-soluble mahogany sulfonic acids are condensed-ring compounds, which condensed-rings may be aromatic or hydroaromatic in nature. Alkyl and/or cycloalkyl substituents may be present in the mahogany sulfonic acids.

The term "oil-soluble sulfonic acids," as used herein, refers to those materials wherein the hydrocarbon portion of the molecule has a molecular weight in the range of about 300 to about 1,000. Preferably, this molecular weight is in the range of about 370 to about 700. These oil-soluble sulfonic acids can be either synthetic sulfonic acids or the so-called mahogany or natural sulfonic acids. The term "mahogany sulfonic acid" is believed to be well understood, since it is amply described in the literature. The term "synthetic sulfonic acids" refers to those materials which are prepared by sulfonation of hydrocarbon feedstocks which are prepared synthetically. The synthetic sulfonic acids can be derived from either alkyl or alkaryl hydrocarbons. In addition, they can be derived from hydrocarbons having cycloalkyl (i.e., napthenic) groups in the side chains attached to the benzene ring. The alkyl groups in the alkaryl hydrocarbons can be straight or branched chain. The alkaryl radical can be derived from benzene, toluene, ethyl benzene, xylene isomers, or naphthalene.

An example of a hydrocarbon feedstock which has been particularly useful in preparing synthetic sulfonic acids is a material known as postdodecylbenzene. Postdodecylbenzene is a bottoms product of the manufacture of dodecylbenzene. The alkyl groups of postdodecylbenzene are branched chain. Postdodecylbenzene consists of monoalkylbenzenes and dialkylbenzenes in the approximate mole ratio of 2:3 and has typical properties as follows:

| | |
|---|---|
| Specific gravity at 38 degrees C | 0.8649 |
| Average molecular weight | 385 |
| Percent sulfonatable | 88 |
| ASTM D-158 Engler: | |
| I.B.P., degrees F | 647 |
| 5 degrees F | 682 |
| 50 degrees F | 715 |
| 90 degrees F | 760 |
| 95 degrees F | 775 |
| F.B.P. degrees F | 779 |
| Refractive index at 23 degrees C | 11.4900 |
| Viscosity at: | |
| −10 degrees C, centistokes | 2800 |
| 20 degrees C, centistokes | 280 |
| 40 degrees C, centistokes | 78 |
| 80 degrees C, centistokes | 18 |
| Aniline point, degrees C | 69 |
| Pour Point, degrees F | −25 |

An example of another hydrocarbon feedstock which is particularly useful in preparing synthetic sulfonic acids is a material referred to as "dimer alkylate." "Dimer alkylate" has a long branched-chain alkyl group. Briefly described, dimer alkylate is prepared by the following steps:

1. dimerization of a suitable feedstock, such as cat poly gasoline; and
2. alkylation of an aromatic hydrocarbon with the dimer formed in step (1).

Preferably, the dimerization step uses a Friedel-Crafts alkylation sludge as the catalyst. This process and the resulting product are described in U.S. Pat. No. 3,410,925.

An example of another hydrocarbon feedstock which is particularly useful for preparing synthetic sulfonic acids which can be used in my invention is a material which I refer to as "NAB Bottoms." NAB Bottoms are predominantly di-n-alkyl aromatic hydrocarbon wherein the alkyl groups contain from 8 to 18 carbon atoms. They are distinguished primarily from the preceding sulfonation feedstocks in that they are straight chain and contain a large amount of disubstituted material. A process of preparing these materials and the resulting product are described in application Ser. No. 62,211, filed Aug. 7, 1970, and being a continuation-in-part of application Ser. No. 529,284, filed Feb. 23, 1966, and now abandoned. Application Ser. Nos. 62,211 and 529,284 have the same assignee as the present application. The product is also described in U.S. Pat. No. 3,288,716, which is concerned with an additional use for the product, other than sulfonation feedstock. Another process of preparing these materials is described in application Ser. No. 53,352, filed Aug. 6, 1970, and having the same assignee as the present application. Application Ser. No. 53,352 is a continuation-in-part of application Ser. No. 529,284. Still another process of preparing a di-n-alkaryl product is described in application Ser. No. 104,476, filed Jan. 7, 1971, which is a continuation-in-part of application Ser. No. 521,794, filed Jan. 20, 1966, and now abandoned.

In order to make my disclosure even more complete, U.S. Pat. No. 3,410,925 and application Ser. Nos. 53,352; 62,211 and 104,476, are made a part of this disclosure.

In addition to the sulfonic acids derived from the foregoing described hydrocarbon feedstock, examples of other suitable sulfonic acids include the following: mono- and poly-substituted naphthalene sulfonic acid, dinonyl napthalene sulfonic acid, diphenyl ether sulfonic acid, napthalene disulfide sulfonic acid, dicetyl thianthrene sulfonic acid, dialauryl betanaphthol sulfonic acid, dicapryl nitronaphthalene sulfonic acid, unsaturated paraffin wax sulfonic acid, hydroxy substituted paraffin wax sulfonic acid, tetraamylene sulfonic acid, mono- and poly-chlorosubstituted paraffin wax sulfonic acid, nitrosoparaffin wax sulfonic acid, cycloaliphatic sulfonic acid such as lauryl-cyclohexyl sulfonic acid, mono- and poly-wax-substituted cyclohexyl sulfonic acid, and the like.

The corresponding hydrocarbon sulfonic acid is usually prepared by treating the hydrocarbon with concentrated sulfuric acid, fuming sulfur acid or sulfur trioxide. The sulfonation of hydrocarbons is well known and details need not be given. The sulfonic acid may also be purified by any suitable means: i.e., treatment with inorganic base, ion exchange, water washing and the like.

As previously stated the oil-soluble sulfonic acid is often diluted with a volatile solvent. The volatile solvent can be any suitable hydrocarbon, preferably a low boiling hydrocarbon such as hexane or naphtha which may readily be removed from the metal sulfonate product when desired.

With respect to the types of nonvolatile carriers which may be utilized in the process a wide variety of materials have been found suitable for such usage. The principal requisites desired in the nonvolatile carrier are that it will dissolve the dispersing agents utilized in the process, and that such solutions will be relatively stable when the basic metallic compounds are peptized in the dispersion by the dispersing agent. Examples of such nonvolatile carriers which may be employed include mineral lubricating oil obtained by any of the conventional refining procedures; vegetable oils, such as corn oil, cotton-seed oil, castor oil, etc; animal oil, such as lard oil, sperm oil, etc; and synthetic oils such as polymers of propylene, polyoxyalkylenes, polyoxypropylene, dicarboxylic acid esters, such as esters of adipic and azelaic acids with alcohols such as butyl, 2-ethyl hexyl and dodecyl alcohols, and esters of acids of phosphorus, such as diethyl ester of decanephosphonic acid and tricresyl phosphate. The preferred nonvolatile carriers are liquid lubricating oils, either mineral or synthetic. In addition, sulfonic acid stock such as previously described hereinabove can be employed as the nonvolatile carrier. If desired, the nonvolatile carriers may be diluted with a solvent to reduce the viscosity. Suitable solvents include petroleum naphtha or hydrocarbons, such as hexane, heptane, octane, benzene, toluene, or xylene.

The alcohols which are suitable for use in the process of the present invention are those which have a boiling point of at least 75° C. and in which the reactants have an appreciable miscibility. Those alcohols found suitable include alcohols having from 3 to about 6 carbon atoms, monoethers of ethylene glycol containing not more than 8 carbon atoms, and monoethers of diethylene glycol containing not more than 8 carbon atoms. Preferred glycol ethers are the monoethyl ether of ethylene glycol and the monomethyl ether of ethylene glycol. These materials are available commercially under the trademarks "CELLOSOLVE" and "methyl CELLOSOLVE." The monoethyl ether of diethylene glycol is available commercially under the trademark "CARBITOL."

The monoethers of ethylene glycol are also known as alkoxy alkanols, and more specifically as alkoxy ethanols. These materials have the generic formula, $ROCH_2CH_2OH$, where R is a $C_1$ to $C_6$ hydrocarbon group. Similarly, the monoalkylether of diethylene glycol has the generic formula, $HOCH_2CH_2OCH_2CH_2OR$, where R is a $C_1$ to $C_4$ hydrocarbon group.

The polyamine compounds which may be employed in the production of the oil-soluble anionic metal sulfonates can be any suitable polyamine compound having a molecular weight of at least 100.

Especially desirable results have been obtained wherein the polyamine compound is the diamine 1,3-diaminopropane having an alkyl moiety selected from the group consisting of N-coco, N-tallow, N-soya and N-oleyl. The compound 1,3-diaminopropane can be represented by the general formula $R-NH(C_3H_6NH_2)$ wherein R is an alkyl group representing the coco, tallow, soya or oleyl moiety. These diamines are available commercially under the tradename DUOMEEN C, T, O and S.

Other suitable polyamines include tetraethylene pentamine and similar polyamine types containing primary and/or secondary amine groups. Further suitable polyamines can be represented by the general formulas $R(NH_2)_2$ and $R(NH-C_3H_6NH_2)_2$ wherein R is an alkyl radical derived from the dimerization of a $C_{18}$ unsaturated fatty acid. Another group of suitable polyamine compounds can be represented by the general formula $R-N-(C_3H_6NH_2)_2$ wherein R is an alkyl radical derived from tallow, oleyl and lauryl fatty acids.

In order to more fully illustrate the nature of the present invention, the following examples are given. However, it is to be understood that the examples are for illustrative purposes only and are not intended to unduly limit or restrict the scope of the present invention. In each example the sulfonic acid was derived from an alkyl-aromatic which was predominantly di-n-alkylbenzenes having a molecular weight of about 420, unless otherwise specified.

EXAMPLE 1

To a creased one-liter flask was charged 25 ml of water, 31.9 grams of N-coco-1,3-diaminopropane and then mechanically agitated. Heat was applied and the reaction was taken to 40°–50° C., whereupon 100.0 grams of sulfonic acid were charged over a period of 15 minutes and the reaction taken to 50°–60° C. where 3.5 grams of arsenic acid anhydride were charged and the reaction refluxed at a temperature of 75°–80°C. and refluxed for 2 hours, volatiles were taken overhead to 120°–125°C. and the reaction was again refluxed for 2 hours, then the volatiles were taken overhead to a pot temperature of 140° C.; 40 grams of 80 pale oil were charged at about 140° C. The product was then stripped with $N_2$ gas for 15 minutes and filtered through Hyflo. The bright fluid product was analyzed and found to contain 2.0 weight percent arsenic.

EXAMPLE 2

An experiment was conducted employing the procedure of Example 1 except that 7.9 grams of molybdic acid anhydride ($MoO_3$) were substituted for the 3.4 grams of $As_2O_5$. The charge employed in this experiment was as follows:

| | |
|---|---|
| 100.0 grams | Sulfonic Acid |
| 31.9 grams | N-Coco-1,3-diaminopropane |
| 7.9 grams | Molybdic Acid Anhydride ($MoO3$) |
| 40 grams | 80 Pale Oil |
| 150 ml | Methyl CELLOSOLVE |
| 25 ml | Water |

The bright and fluid product produced was filtered as in Example 1 and found to contain 3.9 weight percent molybdenum.

EXAMPLE 3

An experiment was conducted employing the procedure of Example 1 except that 68.2 grams of a primary mono fatty amine (commercially available under tradename ARMEEN T) was substituted for the diamine. The charge employed in this experiment was as follows:

| | |
|---|---|
| 100.0 grams | Sulfonic Acid |
| 68.2 grams | ARMEEN T (primary mono fatty amine) |
| 3.4 grams | Arsenic Anhydride ($As_2O_5$) |
| 40 grams | 80 Pale Oil |
| 150 ml | Methyl CELLOSOLVE |
| 25 ml | Water |

The product produced was filtered as in Example 1 and was initially bright and fluid; but after overnight storage at ambient temperature the filtrate turned hazy and solids were observed.

Having thus described the invention, I claim:

1. A process of producing a reaction product of a polyamine compound, an oil-soluble sulfonic acid and arsenic oxide or a hydrate thereof comprising:
   a. admixing said arsenic oxide or hydrate thereof and said oil-soluble sulfonic acid with said polyamine compound, said sulfonic acid being present in sufficient amount to neutralize at least one amine group of said polyamine, and at least one amine group of said polyamine being available to react with said arsenic oxide or hydrate thereof;
   b. agitating and heating the resulting mixture to the reflux temperature of said mixture for a period of time sufficient to allow formation of said reaction product; and
   c. recovering said reaction product.

2. The process of claim 1 wherein said oil-soluble sulfonic acid is diluted with from about 5 to 75 weight percent of an inert volatile solvent and said reflux temperature is in the range of about 60° to 125° C.

3. The process of claim 2 wherein said inert volatile solvent is a low boiling hydrocarbon selected from the group consisting of hexane and naptha.

4. The process of claim 1 wherein said reaction mixture is maintained at its reflux temperature for a period of time ranging from about 0.5 to 12 hours.

5. The process of claim 4 which includes the step of admixing from about 5 to about 75 weight percent water, based on the amount of sulfonic acid employed, to said mixture prior to same being refluxed.

6. The process of claim 4 which includes the step of admixing from about 50 to about 300 weight percent of a high boiling alcohol, based on the amount of sulfonic acid employed, to said mixture prior to same being refluxed.

7. The process of claim 1 wherein the refluxed mixture is stripped of volatile components by heating said refluxed mixture to a temperature within the range of about 125° to 175° C. and includes the step of admixing from about 10 to 300 weight percent of a nonvolatile organic carrier component based on the amount of sulfonic acid employed, to said reflux mixture during refluxing of same.

8. The process of claim 7 which includes the additional purification steps of stripping the product with an inert gas selected from the group consisting of nitrogen, carbon dioxide, air and mixtures thereof for a period of time ranging from about 0.2 to 6 hours and filtering the gas stripped product through an inert absorbent material selected from the group consisting of alumina, diatomaceous earth and pumice.

9. The process of claim 1 wherein the polyamine compound has a molecular weight of at least 100.

10. The process of claim 9 wherein said oil-soluble sulfonic acid was derived from an alkyl-aromatic compound which was predominantly di-n-alkylbenzenes having a molecular weight of about 420, and said nonvolatile carrier component is pale oil.

11. The process of claim 10 wherein said nonvolatile carrier is diluted with a solvent selected from the group consisting of petroleum naptha, hexane, heptane, octane, benzene, toluene, and xylene.

12. The process of claim 9 wherein said polyamine compound is 1,3-diaminopropane having an alkyl moiety selected from the group consisting of N-coco, N-tallow, N-soya, and N-oleyl.

* * * * *